2-ALKYL-5-ALKYL SULFONY 1-4,6-DIHALOPYRIMIDINES AND THE PRODUCTION THEREOF

[75] Inventors: Karl Hoegerle, Basel; Kurt Ohnemus, Riehen, both of Switzerland

[73] Assignee: Ciba-Geigy Corporation, Ardsley, N.Y.

[21] Appl. No.: 329,169

[22] Filed: Dec. 10, 1981

[30] Foreign Application Priority Data

Dec. 17, 1980 [CH] Switzerland ............... 9301/80

[51] Int. Cl.³ .................................. C07D 239/40
[52] U.S. Cl. ................................ 544/298; 8/663
[58] Field of Search ............................ 544/298

[56] References Cited

U.S. PATENT DOCUMENTS 4,287,342 9/1981 Hoegerle ..................... 544/298

FOREIGN PATENT DOCUMENTS 1273914 5/1972 Fed. Rep. of Germany .
24260 2/1981 European Pat. Off. ........... 544/298

OTHER PUBLICATIONS

Chemical Abstracts, Reg. #25096-70-2 (1975).

Primary Examiner—Robert Gerstl
Attorney, Agent, or Firm—Joseph G. Kolodny

[57] ABSTRACT

The invention discloses novel 2-alkyl-5-alkylsulfonyl-4,6-dihalopyrimidines of the formula I

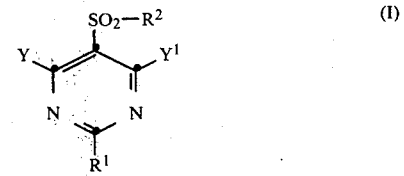

wherein each of $R^1$ and $R^2$ independently is straight chain or branched chain $C_1$–$C_5$alkyl, and each of Y and $Y^1$ is chlorine, fluorine or bromine. The compounds of the formula (I) can be obtained e.g. by reacting a 2-alkyl-4,6-dihydroxypyrimidine, in the presence of a chlorinating, brominating and/or fluorinating agent, with a dialkyl sulfoxide, and then oxidizing the compound obtained. The compounds of the formula (I) are valuable intermediates which are suitable e.g. for the manufacture of reactive dyes.

5 Claims, No Drawings

2-ALKYL-5-ALKYL SULFONY 1-4,6-DIHALOPYRIMIDINES AND THE PRODUCTION THEREOF

The present invention relates to novel 2-alkyl-5-alkylsulfonyl-4,6-dihalopyrimidines which are suitable e.g. for the manufacture of reactive dyes, to processes for the production of these novel compounds, and also the novel intermediates obtained.

It is known that 2-alkylsulfonyl-4-halo-6-alkylpyrimidines can be used for obtaining reactive dyes. The formation of the reactive dye takes place via the halogen atom in the 4-position; and the alkylsulfonyl group in the 2-position acts as leaving group in the formation of the covalent bond between dye and substrate (q.v. for example U.S. Pat. No. 3,853,840). Reactive dyes having an alkyl group in the 6-position and an alkylsulfonyl group in the 2-position of the pyrimidine ring are suitable for dyeing and printing cellulosic materials. These dyes are fixed on the fibre exclusively by the alkylsulfonyl group as leaving group. It is the object of this invention to provide novel reactive components which, after reaction with a chromophore to form a reactive dye, afford a wider range of application.

There have now been found novel 2-alkyl-5-alkylsulfonyl-4,6-dihalopyrimidines which can be used for the manufacture of reactive dyes that are suitable both for use in printing and in pad dyeing methods. The function of the halogen atoms in these compounds is to form the dye/reactive component bond and to fix the reactive dye on the fibre. The alkylsulfonyl group in the 5-position activates the halogen atoms but does not itself participate in the reactions.

Accordingly, the present invention provides novel 2-alkyl-5-alkylsulfonyl-4,6-dihalopyrimidines of the formula I

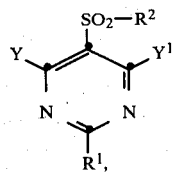
(I)

wherein each of $R^1$ and $R^2$ independently is straight chain or branched chain $C_1-C_5$ alkyl, and each of Y and $Y^1$ independently is chlorine, fluorine or bromine.

Examples of alkyl groups $R^1$ and $R^2$ are: methyl, ethyl, n-propyl, isopropyl, n-butyl, sec-butyl, tert-butyl, n-pentyl, 2- and 3-pentyl.

Y and $Y^1$ are preferably the same and are chlorine, fluorine or bromine. Particularly preferred compounds of the formula I are those in which each of Y and $Y^1$ is chlorine or fluorine, $R^1$ is methyl, ethyl or isopropyl, and $R^2$ is methyl or ethyl. The most preferred compounds of the formula I are those in which each of Y and $Y^1$ is chlorine or fluorine and each of $R^1$ and $R^2$ is methyl.

Examples of specific compounds of the formula I are:
2-methyl-5-methylsulfonyl-4,6-dichloro-, -4,6-dibromo- and -4,6-difluoropyrimidine,
2-ethyl-5-methylsulfonyl-4,6-dichloro- and -4,6-difluoropyrimidine,
2-methyl-5-ethylsulfonyl-4,6-dichloro- and -4,6-difluoropyrimidine,
2-n-propyl-5-methylsulfonyl-4,6-dichloro- and -4,6-difluoropyrimidine,
2-isopropyl-5-methylsulfonyl-4,6-dichloro-, -4,6-dibromo -and -4,6-difluoropyrimidine,
2-methyl-5-methylsulfonyl-2-chloro-4-fluoropyrimidine,
2-n-butyl-5-ethylsulfonyl-4,6-dichloro- and -4,6-difluoropyrimidine,
2-n-pentyl-5-methylsulfonyl-4,6-dichloro- and -4,6-difluoropyrimidine,
2-methyl-5-n-propylsulfonyl-4,6-dichloro- and -4,6-difluoropyrimidine,
2-methyl-5-isopropylsulfonyl-4,6-dichloro- and -4,6-difluoropyrimidine,
2-methyl-5-n-butylsulfonyl-4,6-dichloro- and -4,6-difluoropyrimidine,
2-ethyl-5-ethylsulfonyl-4,6-dichloro- and -4,6-difluoropyrimidine.

The compounds of the formula I can be prepared e.g. by (a) reacting a salt of a dianion of the formula II

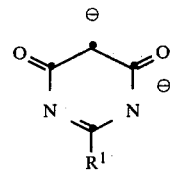
(II)

with a compound of the formula III

(III)

to a compound of the formula IV

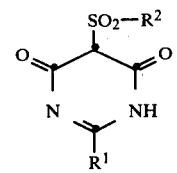
(IV)

or to a salt thereof;

(b) reacting a compound of the formula IIa

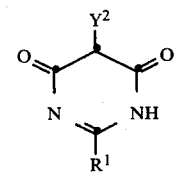
(IIa)

in the presence of a polar solvent, with a compound of the formula IIIa

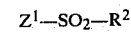
(IIIa)

to a compound of the formula IV, and reacting the compound of the formula IV obtained in accordance with (a) or (b), or the salt thereof, by treatment with a chlorinating, brominating and/or fluorinating agent, to a compound of the formula I; or (c) reacting a compound of the formula IIb

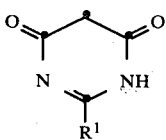

(IIb)

in the presence of a chlorinating, brominating and/or fluorinating agent, with a compound of the formula IIIb $(R^2)_2SO$           (IIIb)

to a compound of the formula V

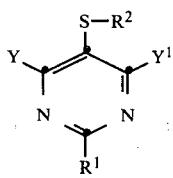

(V)

oxidising said compound of the formula V with a mild oxidising agent to a compound of the formula I and, if desired, subjecting the compound of the formula I, wherein one of Y and $Y^1$ is chlorine and the other is chlorine, bromine or fluorine, to transhalogenation. In the formulae above, $R^1$, $R^2$, Y and $Y^1$ are as defined for formula I, $Y^2$ is chlorine, fluorine or bromine, with chlorine being preferred, Z is a halogen atom such as chlorine, fluorine or bromine, with chlorine being preferred, or is $-O-SO_2-R^2$, and $Z^1$ is the cation of an alkali metal or alkaline earth metal, preferably the sodium or potassium cation.

It is preferred to obtain the compounds of the formula I by process variant (c), i.e. by reaction of a compound of the formula IIb, in the presence of a chlorinating, brominating and/or fluorinating agent with a compound of the formula IIIb, and subsequent oxidation and, if desired, transhalogenation.

The compounds of the formula II can exist in different resonance structures, whereas the compounds of the formulae IIa, IIb and IV, and the salts thereof, can exist in several tautomeric forms. For the sake of simplicity, these compounds are illustrated in the formulae in only one of these resonance structures or tautomeric forms. It must be clearly emphasised, however, that throughout this specification, including the claims, mention of the above compounds is always to be understood as referring to any one of their resonance structures or tautomeric forms.

The compounds of the formula IV and salts thereof, as well as the compounds of the formula V, are novel and likewise constitute an object of the invention. In these formulae, $R^1$, $R^2$, Y and $Y^1$ advantageously have the preferred meanings given above.

Suitable salts of dianions of the formula II or of compounds of the formula IV are salts with inorganic or organic bases, e.g. alkali metal salts and alkaline earth metal salts as well as quaternary ammonium salts such as tetraalkylammonium salts or benzyltrialkylammonium salts containing 1 to 8, preferably 1 to 4, carbon atoms in each alkyl moiety. Examples of such salts are the lithium, sodium, potassium and calcium salts, benzyltrimethylammonium, benzyltriethylammonium and tetramethylammonium salts. Preferred salts are tetraalkylammonium and benzyltrialkylammonium salts containing 1 to 4 carbon atoms in each alkyl moiety, preferably tetraethylammonium and benzyltriethylammonium salts, and alkali metal salts, preferably sodium and potassium salts.

The preparation of the above salts can be carried out in a manner known per se before the further reaction or in the reaction medium itself, i.e. in situ.

The starting materials of the formulae II, IIa, IIb, III, IIIa and IIIb are known or they can be prepared by methods which are known per se.

Examples of suitable starting materials of the formulae III, IIIa and IIIb are: methanesulfonyl chloride, methanesulfonyl bromide, ethanesulfonyl chloride, propanesulfonyl chloride, isopropanesulfonyl chloride, n-butanesulfonyl chloride, sec-butanesulfonyl chloride, n-pentanesulfonyl chloride, 2- and 3-pentanesulfonyl chloride; sodium methanesulfinate, potassium methanesulfinate and calcium methanesulfinate, sodium and potassium ethanesulfinate, sodium and potassium propanesulfinate, sodium and potassium isopropanesulfinate, sodium and potassium n-butanesulfinate, sodium and potassium sec-butanesulfinate, sodium and potassium tert-butanesulfinate, sodium and potassium n-pentanesulfinate, sodium and potassium 2- and 3-pentanesulfinate; dimethyl sulfoxide, diethyl sulfoxide, di-sec-butylsulfoxide, di-n-pentylsulfoxide, di-2-pentyl sulfoxide and di-3-pentyl sulfoxide.

It is advantageous to use compounds of the formulae II, IIa, IIb, III, IIIa or IIIb, or salts of compounds of the formula II, wherein $R^1$ and $R^2$ have the preferred meanings given above, Z is a chlorine atom, and $Z^1$ is the sodium or potassium cation.

The reaction of the salts of dianions of the formula II with the compounds of formula III is conveniently carried out in the presence of a strong inorganic or organic base. Examples of suitable bases are: hydroxides, amides and hydrides of alkali metals or alkaline earth metals, and alkyl lithium compounds, e.g. methyl lithium, n-butyl lithium, or lithium dialkyl amines, e.g. lithium diisopropyl amide.

The above reaction can be carried out in aqueous medium, in an inert organic solvent or in a mixture of different inert organic solvents, in a mixture of water and one or more inert organic solvents, or also in a solvent two-phase system. As organic solvents it is preferred to use aprotic polar solvents. Suitable solvents of this kind are e.g. N,N-dialkyl amides of aliphatic monocarboxylic acids containing 1 to 3 carbon atoms in the acid moiety, such as N,N-dimethyl formamide, N,N-dimethyl acetamide and N,N-diethyl acetamide; aliphatic and cycloaliphatic ketones such as acetone, methyl ethyl ketone, cyclopentanone and cyclohexanone; cyclic amides such as N-methyl-2-pyrrolidone, N-acetyl-2-pyrrolidone, N-methyl-ε-caprolactam; dialkyl sulfoxides such as dimethyl sulfoxide and diethyl sulfoxide; and pyridine.

Suitable solvent/two-phase systems are, in particular, water/organic solvent systems, e.g. water/methylene chloride or water/toluene.

The preferred reaction is that in aqueous medium at or above a pH value of 11, preferably in the range from 11.5 to 12.5, in which reaction the salts of dianions of the formula II are usually formed in situ. The preferred base employed in the reaction is sodium hydroxide or potassium hydroxide.

For the reaction in organic medium it is advantageous to use a non-aqueous base such as an alkyl lithium, e.g butyl lithium, or the amide or hydride of an alkali metal, e.g. lithium diisopropyl amide or sodium hydride.

The reaction of the salts of dianions of the formula II with the compounds of the formula III is conveniently carried out in the temperature range from $-20°$ to $+100°$ C., preferably from $+10°$ to $+50°$ C., and, if desired, in the presence of a phase transfer catalyst. Examples of phase transfer catalysts which can be used are ammonium or sulfonium salts, preferably tetraalkylammonium or benzyltrialkylammonium halides, most preferably chlorides, such as benzyltriethylammonium chloride.

When the reaction is complete, the compounds of the formula IV are obtained direct or after acidifying the reaction solution, e.g. with concentrated hydrochloric acid or concentrated sulfuric acid, in the form of salts, and some are also obtained in the form of the free acid. The compounds can be purified by recrystallization from water. If desired, the free 5-alkylsulfonyl derivatives can be obtained from the salts in a manner which is known per se, e.g. by treating the salts with strongly acid ion exchangers, such as synthetic resins which contain $SO_3^-$ groups. On the other hand, it is also possible to convert the compounds of formula IV, in a manner known per se, into salts of the above mentioned kind, or to convert the salts obtained on completion of the reaction into other salts.

As polar solvents for the reaction of compounds of the formula IIa with the alkali metal sulfinates or alkaline earth metal sulfinates of the formula IIIa there can be used e.g. N,N-disubstituted amides of aliphatic monocarboxylic acids containing 1 to 3 carbon atoms in the acid moiety, such as N,N-dimethyl formamide, N-N-dimethyl acetamide, N,N-diethyl acetamide, N-methyl-N-phenyl acetamide and N,N-dimethylmethoxy acetamide; cyclic amides such as N-methyl-2-pyrrolidone, N-acetyl-2-pyrrolidone and N-methyl-$\epsilon$-caprolactam; tetraalkyl ureas such as tetramethyl urea; or dialkyl sulfoxides such as dimethyl sulfoxide and diethyl sulfoxide; or mixtures of such solvents. Preferred solvents are dialkyl sulfoxides, in particular dimethyl sulfoxide or diethyl sulfoxide. The reaction temperature is preferably in the range from 50° to 200° C., preferably from 80° to 150° C.

Examples of suitable chlorinating, brominating and-/or fluorinating agents for converting the compounds of formula IV, or salts thereof, into compounds of the formula I, or for the reaction of compounds of the formula IIb with compounds of the formula IIIb, are: phosphorus oxychloride, phosphorus oxybromide or phosphorus oxyfluoride; methylphosphonic dichloride ($CH_3POCl_2$), phenylphosphonic dichloride ($C_6H_5POCl_2$), phosgene, thionyl bromide, thionyl chloride and $SF_4$. Mixtures of different compounds of this kind, e.g. mixtures of phosphorus oxychloride, oxybromide or oxyfluoride, or else halogenating agents which split off water and contain different halogen atoms, e.g. so-called mixed thionyl halides such as SOClF or SOBrCl, can also be used. These reactions yield compounds of the formula I or V in which Y and $Y^1$ have different meanings. It si preferred to use a chlorinating agent, in particular phosphorus oxychloride.

It is generally convenient to carry out the conversion of compounds of the formula IV, or salts thereof, into compounds of the formula I in the presence of a reaction inductor. Suitable inductors are e.g. aliphatic or aromatic tertiary bases such as triethylamine, N,N-dimethyl aniline, N,N-diethyl aniline, or N,N-disubstituted amides or aliphatic carboxylic acids, such as N,N-dimethyl formamide and N,N-dimethyl acetamide. These inductors are normally employed in an amount of 1-200 mol.%, based on the amount of compound of the formula IV or salt thereof. It is preferred to use equimolar amounts of inductor.

The above reactions with a chlorinating, brominating and/or fluorinating agent in accordance with process variants (b) or (c), are preferably conducted in an inert organic solvent. Examples of suitable solvents are aromatic hydrocarbons such as xylenes, toluene, chlorobenzene or nitrobenzene, as well as chlorinated aliphatic or cycloaliphatic hydrocarbons such as dichloromethane, trichloroethylene, carbon tetrachloride and cyclohexyl chloride.

It is also possible to use an excess of chlorinating, brominating and/or fluorinating agent, preferably phosphorus oxychloride, as solvent, in particular for converting compounds of the formula IV, or salts thereof, into compounds of the formula I.

The introduction of chlorine, bromine and/or fluorine in accordance with process variant (b) is conveniently carried out in the temperature range from 20° to 250° C., preferably from 50° to 150° C.

The reaction of compounds of the formula IIb, in the presence of a chlorinating, brominating and/or fluorinating agent, with a compound of the formula IIIb, is preferably carried out in the temperature range from 0° to 150° C. and in the presence of an inert organic solvent, preferably a chlorinated aliphatic hydrocarbon such as dichloromethane.

Examples of mild oxidising agents for the reaction of compounds of the formula V to compounds of the formula I are peracetic acid, 3-chloroperbenzoic acid, perbenzoic acid, hydrogen peroxide, sodium iodate, perlauric acid, iodobenzodichloride, N-chlorosuccinimide, N-bromosuccinimide and chlorine. The above reaction is conveniently conducted in an inert solvent. Examples of suitable solvents are dichloromethane, chloroform, acetic acid, acetic anhydride and water, or mixtures thereof. The oxidation temperature is in general in the range from $-50°$ to $+50°$ C. Preferred oxidising agents are peracetic acid and 3-chloroperbenzoic acid. Similar oxidation reactions are described e.g. in Tetrahedron Letters, 1973, page 2365, and reference is also made to "Organic Compounds of Bivalent Sulfur", Vol. 2, page 4 (Chemical Publishing Co., New York, 1960).

Compounds of the formula I obtained in accordance with process variants (a), (b) and (c), wherein one of Y and $Y^1$ is chlorine and the other is chlorine, bromine or fluorine, can, if desired, be reacted with a brominating or fluorinating agent, such as phosphorus tribromide, anhydrous hydrogen fluoride, an alkali metal fluoride or potassium fluorosulfinate, until one or both chlorine atoms are replaced. Thus, for example, compounds of the formula I, wherein each of Y and $Y^1$ are chlorine, can be converted into the bromo or fluoro analogs, by converting these compounds of the formula I by reaction with phosphorus tribromide, which can also act as solvent, into the corresponding 4,6-dibromopyrimidine derivatives, or by converting compounds of the formula I, wherein Y and $Y^1$ are both chlorine, by reaction with anhydrous hydrogen fluoride, potassium fluorosulfinate or an alkali metal fluoride, undiluted or in the presence of a high boiling aprotic organic solvent, into the corresponding 4,6-difluoro compounds. Examples of suitable solvents for these transhalogenation reactions are aromatic hydrocarbons such as toluene and xylenes; N,N-dialkyl amides of aliphatic monocarboxylic acids of the kind previously specified above, such as N,N-dimethyl formamide and N,N-dimethyl acetamide; cyclic ethers and cyclic amides, such as tetrahydrofurane, tetrahydropyrane, N-methyl-2-pyrrolidone and N-acetyl-2-pyrrolidone; hexamethylphosphoric triamide (hexametapol); N,N,N',N'-tetramethyl urea, and tetrahydrothiophene dioxide (sulfolane). The reaction temperatures for the transhalogenation are preferably from 20° to 250° C., most preferably from 50° to 150° C.

The compounds of the formula I and the intermediates of the formula IV, or the salts thereof, and the intermediates of the formula V, can be obtained in good yield by the process of the invention and under mild reaction conditions.

As already mentioned, the compounds of the formula I are valuable intermediates which are suitable, in particular, for the manufacture of reactive dyes. Condensation of compounds of the formula I, especially compounds of the formula I in which $R^1$, $R^2$, Y and $Y^1$ have the preferred meanings assigned to them above, with dyes which contain amino groups, yield fibre-reactive dyes which have a high degree of fixation.

The reactive dyes obtained are suitable for dyeing and printing a very wide range of materials, such as silk, leather, wool, polyamide and polyurethane fibres, and especially cellulosic materials of fibrous structure such as linen, cellulose, regenerated cellulose and, in particular, cotton. They are suitable for dyeing by the pad-dyeing process, in which the goods are impregnated with aqueous and, if appropriate, also with salt-containing dye solutions, and the dyes are fixed after treatment with alkali or in the presence of alkali, with or without the application of heat.

They are also suitable for printing, in particular on cotton, and also for printing nitrogen-containing fibres, for example wool, silk, or blends containing wool.

The invention is illustrated by the following Examples.

Example 1: Preparation of 2-methyl-4,6-dihydroxy-5-methylsulfonylpyrimidine (a) 12.6 g (0.1 mole) of 2-methyl-4,6-dihydroxypyrimidine are dissolved in 100 ml of water and 10 ml of 10N aqueous sodium hydroxide. The pH of the solution is 11.7. Then 0.1 g of benzyltriethylammonium chloride is added and 22.9 g (0.2 mole) of methanesulfonyl chloride are added dropwise over about 3 hours. The pH is kept at 11.5 to 12 with 5N aqueous sodium hydroxide and the temperature is kept at 25°–30° C. by cooling. The reaction solution is stirred for another 2 hours at room temperature (20°–25° C.), and then the pH is adjusted to 5 by addition of about 15 ml of 10N hydrochloric acid. Precipitated unreacted starting material is removed by filtration and the filtrate is evaporated to dryness in vacuo. The crude product, which still contains starting material and sodium methylsulfonate, is thoroughly dried in a high vacuum. An analytically pure sample of the compound does not melt at 330° C., but decomposes slowly while discolouring brownish black from about 280° C. The compound is characterised by microanalysis and also by IR and $^{13}C$ spectra.

Analysis: Calculated C: 35.30%; H: 3.95%; N: 13.72%; O: 31.34%; S: 15.70%. Found C: 35.30%; H: 3.84%; N: 13.86%; O: 31.25%; S: 15.62%.

Most important IR-bands at 1660 cm$^{-1}$, 1634 cm$^{-1}$, 1357 cm$^{-1}$, 1300 cm$^{-1}$, 1136 cm$^{-1}$, 962 cm$^{-1}$, 788 cm$^{-1}$.

$^{13}C$—NMR data: C-2 162.0 ppm, C-4 and C-6 158.3 ppm, C-5 99.1 ppm, $CH_3SO_2$ 44.0 ppm, $CH_3$ in the 2-position 17.8 ppm.

(b) 16 g (0.1 mole) of 2-methyl-5-chloro-4,6-dihydroxypyrimidine and 11.2 g (0.11 mole) of sodium methylsulfinate are stirred in 50 ml of dimethyl sulfoxide for 4 hours at 125°–130° C. The suspension is filtered clear at 90° C. and chloroform is added to the filtrate. The flocculent precipitate is isolated by filtration and well dried, affording 9.4 g of approx. 90% product which is used for the further reaction without being purified.

Example 2: Preparation of 2-methyl-4,6-dichloro-5-methylsulfonylpyrimidine (a) 35 g of dry crude 2-methyl-4,6-dihydroxy-5-methylsulfonylpyrimidine [prepared according to variant (a) or (b) of Example 1] is slowly added to a solution of 12.1 g of N,N-dimethyl aniline in 150 ml of phosphorus oxychloride. The suspension is then slowly heated. The reaction takes place at 80° C. accompanied by vigorous evolution of hydrogen chloride. The suspension is further heated to reflux and kept for 20 hours at this temperature. The phosphorus oxychloride is distilled off, the residue is taken up in dichloromethane, and the solution is washed with ice-water and dried over magnesium sulfate. The dichloromethane is distilled off and 2-methyl-4,6-dichloropyrimidine is removed by distillation at a bath temperature of 130° C./26 mbar. The product is then sublimed at a bath temperature of 140° C./0.9 mbar. Crystallisation from carbon tetrachloride gives pure 2-methyl-4,6-dichloro-5-methylsulfonylpyrimidine with a melting point of 146°–147° C.

Analysis: Calculated C: 29.89%; H: 2.51%; N: 11.62%; S: 13.30%; Cl: 29.41%. Found: C: 29.81%; H: 2.43%; N: 11.61%; S: 13.05%; Cl: 29.40%.

(b) 20.9 g (0.1 mole) of 2-methyl-5-methylthio-4,6-dichloropyrimidine are dissolved in a solution of 10 ml of acetic anhydride in 150 ml of acetic acid. With good stirring, 42 g (0.22 mole) of 40% peracetic acid are added dropwise over 1 hour, while keeping the temperature at 40°–45° C. by gentle cooling. The reaction solution is kept for a further 4–5 hours at this temperature, stirred overnight at room temperature, and then cooled to 15° C. The precipitate is isolated by filtration and recrystallised from petroleum ether. The product has a melting point of 138°–140° C. The IR spectrum of the compound obtained is identical with that of the compound obtained in (2a).

The starting material used in (b) is prepared as follows:

37.8 g (0.3 mole) of 2-methyl-4,6-dihydroxypyrimidine are suspended in 150 ml of phosphorus oxychloride and 100 ml of dichloromethane. Then 26.6 g (0.34 mole) of dimethyl sulfoxide are added dropwise over 2½ hours at 20°–25° C., while cooling. The reaction mixture is stirred overnight at room temperature and then slowly heated. Hydrogen chloride starts to evolve at 50°–55° C. while at the same time the dichloromethane is distilled off, and the solution is then refluxed for 12 hours. The contents of the flask are then poured into water and the temperature is kept at about 25° C. by adding ice. The product is extracted with dichloromethane and the solution is dried over magnesium sulfate and concentrated. The residue is distilled in a high vacuum. The distillate with a boiling point of 50°–64° C./0.13 mbar gives from petroleum ether colourless crystals with a melting point of 59°–60° C.

Analysis: Calculated C: 34.46%; H: 2.89%; N: 13.40%; S: 15.33%; Cl: 33.91%. Found C: 34.52%; H: 2.82%; N: 13.49%; S: 14.96%; Cl: 34.26%.

Example 3:
2-Methyl-5-methylsulfonyl-4,6-difluoropyrimidine

To a solution of 14.5 g (0.06 mole) of 2-methyl-5-methylsulfonyl-4,6-dichloropyrimidine in 400 ml of absolute toluene are added 82 g (0.55 mole) of potassium fluorosulfinate. The suspension is slowly heated to reflux and then kept for 18 hours at the boil. The reaction mixture is then filtered over silica gel and the filter residue is washed repeatedly with dry toluene. The combined filtrates are concentrated at 25°–30° C. in a rotary evaporator and the solid residue (8.8 g) is purified by fractional sublimation at 50°–60° C. in a water jet vacuum. The pure substance has a melting point of 120°–123° C.

Example 4: Preparation of
2-isopropyl-4,6-dichloro-5-ethylsulfonylpyrimidine

To a suspension of 15.4 g (0.1 mole) of 2-isopropyl-4,6-dihydroxypyrimidine in 70 ml of acetic acid and 21 ml of acetic anhydride are added 12.3 g (0.116 mole) of diethyl sulfoxide. The suspension is heated over 2 hours to 95° C. and stirred for 6 hours at this temperature. To the clear cold solution are then added 150 ml of ice-water and the yellow precipitate is isolated by filtration and washed with a small amount of water. The filtrate and wash-water are evaporated to dryness and the residue, together with the precipitate, is dried at 60° C. in a high vacuum. The dried product (21.9 g), 150 ml of phosphorus oxychloride and 12.6 ml of dimethyl aniline are heated to the boil and kept at boiling temperature for 20 hours. The cooled solution is poured into water and kept at about 25° C. with ice. The precipitated dark oil is taken up in methylene chloride and the solution is dried over magnesium sulfate, filtered and concentrated. The residue is fractionated in a high vacuum. At 82°–82° C./0.13 mbar there are obtained 10 g of 2-isopropyl-4,6-dichloro-5-ethylthiopyrimidine which still contains a small amount of 2-isopropyl-4,6-dichloropyrimidine as impurity.

Analysis: Calculated C: 43.04%; H: 4.82%; N: 11.15%; S: 12.76%; Cl: 28.23%. Found C: 42.95%; H: 4.62%; N: 11.18%; S: 11.06%; Cl: 29.72%.

9.8 g (0.039 mole) of 2-isopropyl-4,6-dichloro-5-ethylthiopyrimidine are dissolved in 50 ml of acetic acid and then 15.2 g (0.08 mole) of peracetic acid are slowly added dropwise to this solution. The exothermic reaction is kept in check by cooling at 40° C. After being stirred for 24 hours at room temperature, the clear solution is diluted with 4 times its volume of water. The precipitate is isolated by filtration and taken up in methylene chloride. The aqueous filtrate is extracted with methylene chloride and the extract is washed with sodium bicarbonate solution until neutral. The combined methylene chloride phases are dried over magnesium sulfate, filtered and concentrated to an oil. The residue (6.3 g) is distilled in a high vacuum in a bulb tube. At an oven temperature of 150° C./3;10$^{-2}$ mbar, 5.4 g of 2-isopropyl-4,6-dichloro-5-ethylsulfonylpyrimidine distill in the form of a colourless oil.

Analysis: Calculated C: 38.18%; H: 4.27%; N: 9.89%; S: 11.32%. Found C: 37.85%; H: 4.10%; N: 9.92%; S: 10.91%.

Example 5:
2-Methyl-4,6-dibromo-5-methylsulfonylpyrimidine 8.2 g of 2-methyl-4,6-dihydroxy-5-methylsulfonylpyrimidine and 100 g of phosphorus oxybromide are stirred together for 9 hours at 105°–110° C. The cooled reaction mass is poured, in small portions, into water, while keeping the temperature at 20°–25° C. with ice. The aqueous phase is then extracted with dichloromethane and the extracts are dried over magnesium sulfate. The solvent is distilled off and the residue is sublimed in a high vacuum. The product has a melting point of 161°–162° C.

Example 6

8.76 parts of the dye of the formula

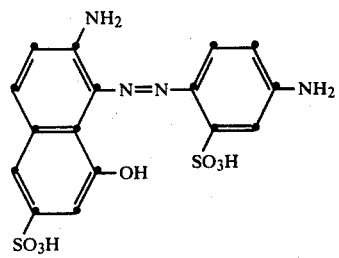

are dissolved neutral in 300 parts of water and to this solution are added 6.68 parts of sodium acetate. With vigorous stirring, a solution of 5.3 parts of 2-methyl-4,6-dichloro-5-methylsulfonylpyrimidine in 40 parts of acetone is added at room temperature to the above solution. When the acylation is complete, the solution is filtered clear and the reactive dye is salted out with sodium chloride, isolated by filtration, buffered with a saturated solution of sodium dihydrogen phosphate and vacuum dried at about 50° C. The reactive dye so obtained dyes cotton in bluish red shades by the pad-steam process.

What is claimed is:

1. A compound of the formula I

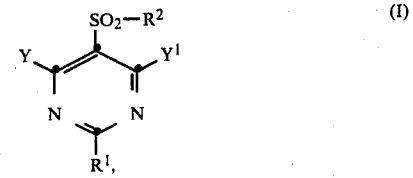

wherein each of $R^1$ and $R^2$ independently is straight chain or branched chain $C_1$–$C_5$alkyl, and each of Y and $Y^1$ independently is chlorine, fluorine or bromine.

2. A compound of the formula I according to claim 1, wherein Y and $Y^1$ are the same and are chlorine, fluorine or bromine.

3. A compound of the formula I according to claim 1, wherein each of Y and $Y^1$ is chlorine or fluorine, $R^1$ is methyl, ethyl or isopropyl, and $R^2$ is methyl or ethyl.

4. A compound of the formula I according to claim 1, wherein each of Y and $Y^1$ is chlorine or fluorine and each of $R^1$ and $R^2$ is methyl.

5. A compound of the formula V

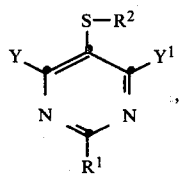
(V)
wherein each of $R^1$ and $R^2$ independently is straight chain or branched chain $C_1$–$C_5$ alkyl, and each of Y and $Y^1$ independently is chlorine, fluorine or bromine.
* * * * *
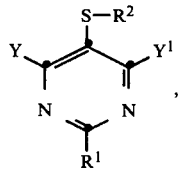
(V)
wherein each of $R^1$ and $R^2$ independently is straight chain or branched chain $C_1$–$C_5$ alkyl, and each of Y and $Y^1$ independently is chlorine, fluorine or bromine.
* * * * *

UNITED STATES PATENT AND TRADEMARK OFFICE
CERTIFICATE OF CORRECTION

PATENT NO. : 4,412,074
DATED : October 25, 1983
INVENTOR(S) : Hoegerle et al.

It is certified that error appears in the above-identified patent and that said Letters Patent is hereby corrected as shown below:

| | |
|---|---|
| 1st Page, Title, lines 1 and 2; Column 1, Title, lines 1 and 2 | Delete "ALKYL SULFONY 1-4,6-" and substitute --ALKYLSUL-FONYL-4,6- -- |
| Col. 8, line 5 | Delete "$CH_3SO_2$" and substitute --$\underline{C}H_3SO_2$" |
| Col. 8, line 5 | Delete "$CH_3$" and substitute --$\underline{C}H_3$-- |
| Col. 12, lines 1-10 | Delete all matter therein as being redundant |

Signed and Sealed this

Twenty-fourth Day of September 1985

[SEAL]

Attest:

Attesting Officer

DONALD J. QUIGG

*Commissioner of Patents and Trademarks—Designate*